(12) United States Patent
DiCosimo et al.

(10) Patent No.: US 6,624,311 B2
(45) Date of Patent: Sep. 23, 2003

(54) ENANTIOSELECTIVE ENZYMATIC AMINOLYSIS OF A RACEMIC 2-ISOXAZOLYLACETATE ALKYL ESTER

(75) Inventors: Robert DiCosimo, Rockland, DE (US); Philip Ma, West Chester, PA (US); Jaan A. Pesti, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/039,972

(22) Filed: Oct. 25, 2001

(65) Prior Publication Data

US 2002/0160465 A1 Oct. 31, 2002

Related U.S. Application Data

(60) Provisional application No. 60/244,092, filed on Oct. 27, 2000.

(51) Int. Cl.$^7$ .............................................. C07D 26/104
(52) U.S. Cl. ...................................... 548/240; 548/243
(58) Field of Search ................................. 548/240, 243

(56) References Cited

U.S. PATENT DOCUMENTS 6,022,977 A    2/2000   Zhang et al.

FOREIGN PATENT DOCUMENTS

WO           99/31264         6/1999

OTHER PUBLICATIONS

Mitin et al, Peptide Synthesis Catalyzed by Papain at Alkaline pH Values, Int. J. Peptide Protein Res., 1984, pp. 528–534, vol. 23.

Nakatsuka et al., Peptide Segment Coupling Catalyzed by the Semisynthetic Enzyme Thiolsubtilisin, J. Am. Chem. Soc., 1987, pp. 3808–3810, vol. 109.

Kato et al., First Stereoselective Synthesis of D–Amino Acid N–Alkyl Amide Catalyzed by D–Aminopeptidase, Tetrahedron, 1989, pp. 5743–5754, vol. 45 No. 18.

Garcia et al., Practical Enzymatic Route to Optically Active 3–Hydroxyamides. Synthesis of 1,3–Aminoalcohols, Tetrahedron: Asymmetry, 1993, pp. 2199–2210, vol 4, No. 10.

Quiros et al., Lipase–Catalyzed Synthesis of Optically Active Amides in Organic Media, Tetrahedron: Asymmetry, 1993, pp. 1105–1112, vol. 4 No. 6.

Puertas et al., Enantioselective Enzymatic Aminolysis and Ammonolysis of Dimethyl 3–Hydroxyglutarate. Synthesis of (R)–4–Amino–3–Hydroxybutanoic Acid, J. Org. Chem., 1996, pp. 6024–6027, vol. 61.

Vorde et al., Resolution of 2–Methylalkanoic Esters: Enantioselective Aminolysis by (R)–1–Phenylethylamine of Ethyl–2–Methyloctanoate Catalyzed by Lipase B From Candida Antarctica, Tetrahedron: Asymmetry, 1996, pp. 1507–1513, vol. 7 No. 5.

Zhang et al., The Chiral Specific Synthesis of DMP754, a Platelet GP IIb/IIIa Antagonist, Tetrahedron Letters, 1996, pp. 4455–4458, vol. 37 No. 26.

Zhang et al., The Enantiospecific Synthesis of an Isoxazoline. A RGD Mimic Platelet GPIIb/IIIa Antagonist, J. Org. Chem., 1997, pp. 2466–2470, vol. 62.

De Castro et al., Lipase–Catalyzed Synthesis of Chiral Amides. A Systematic Study of the Variables That Control the Synthesis, Tetrahedron, 1998, pp. 2877–2892, vol. 54.

Gotor et al., Non–Conventional Hydrolase Chemistry: Amide and Carbamate Bond Formation Catalyzed by Lipases, Bioorganic & Medicinal Chemistry, 1999, pp. 2189–2197, vol. 7.

*Primary Examiner*—Joseph K. McKane
*Assistant Examiner*—Kamal Saeed

(57) ABSTRACT

The present invention relates to a process for the enantioselective enzymatic aminolysis of racemic 2-[3-(4-cyanophenyl)-4,5-dihydro-5-isoxazolyl]acetate ((R/S)-I) by methyl $N_\alpha$-Boc-L-$\alpha,\beta$-diaminoproprionate.p-toluenesulfonic acid. More specifically, this invention pertains to a process for the enantioselective enzymatic aminolysis of racemic isobutyl 2-[3-(4-cyanophenyl)-4,5-dihydro-5-isoxazolyl]-acetate by methyl $N_\alpha$-Boc-L-$\alpha,\beta$-diaminoproprionate.p-toluene sulfonic acid to produce (R)-methyl-3-[[[3-(4-cyanophenyl)-4,5-dihydro-5-isoxazolyl]acetyl]amino]-N-(butoxycarbonyl)-L-alanine, an intermediate in the preparation of roxifiban, an isoxazoline-based platelet glycoprotein IIb/IIIa antagonist which has activity as an antithrombotic agent.

17 Claims, No Drawings

ENANTIOSELECTIVE ENZYMATIC AMINOLYSIS OF A RACEMIC 2-ISOXAZOLYLACETATE ALKYL ESTER

This application claims benefit of U.S. Provisional application No. 60/244,092 filed Oct. 27, 2000.

FIELD OF THE INVENTION

The present invention relates to a process for the enantioselective enzymatic aminolysis of racemic 2-[3-(4-cyanophenyl)-4,5-dihydro-5-isoxazolyl]acetate ((R/S)-I) by methyl $N_\alpha$-Boc-L-α,β-diaminoproprionate.p-toluenesulfonic acid to produce (R)-methyl-3-[[[3-(4-cyanophenyl)-4,5-dihydro-5-isoxazolyl]-acetyl]amino]-N-(butoxycarbonyl)-L-alanine. More specifically, this invention pertains to a process for the enantioselective enzymatic aminolysis of racemic isobutyl 2-[3-(4-cyanophenyl)-4,5-dihydro-5-isoxazolyl]-acetate by methyl $N_\alpha$-Boc-L-α,β-diamino-proprionate.p-toluenesulfonic acid to produce (R)-methyl-3-[[[3-(4-cyanophenyl)-4,5-dihydro-5-isoxazolyl]-acetyl]amino N-(butoxycarbonyl)-L-alanine.

BACKGROUND OF THE INVENTION

The pharmaceutical industry seeks production methods for chiral compounds in high yield and chiral purity. The product of the present invention is useful as a precursor for a pharmaceutical agent of high value in this industry. Specifically, (R)-methyl-3-[[[3-(4-cyanophenyl)-4,5-dihydro-5-isoxazolyl]acetyl]amino]-N-(butoxycarbonyl)-L-alanine ((R,S)-1) is useful as an intermediate in the preparation of roxifiban, a non-peptide platelet glycoprotein IIb/IIIa antagonist which has antithrombotic activity.

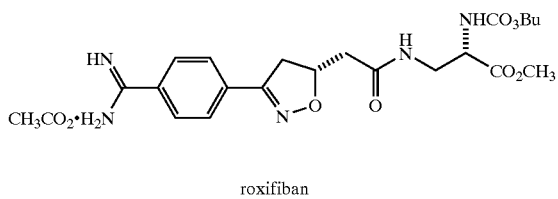

roxifiban

The large-scale preparation of roxifiban has previously been described (Zhang et al., *J. Org. Chem.* 62:2466–2470 (1997); Zhang et al., *Tetrahedron Lett.* 37:4455–4458 (1996)). A key part of this published synthesis is the production of (R,S)-1 in two steps, where racemic isobutyl ester (R/S)-2 is first converted to chiral acid (R)-3 and chiral isobutyl ester (S)-2 via enzymatic resolution in an aqueous reaction mixture (Scheme 1). After isolation from the product mixture of the first step, (R)-3 is reacted in a second step with thionyl chloride and diamine (S)-4, followed by addition of diisopropylethylamine (DIEA) to produce (R,S)-1. In a separate step, recovered (S)-2 is racemized to (R/S)-2 for recycle. This enzymatic resolution-based epimerization sequence provided (R)-3 in 70% yield (after one recycle) from racemate (R/S)-2, and (R)-3 was subsequently converted to (R,S)-1 in 82% yield.

Scheme 1

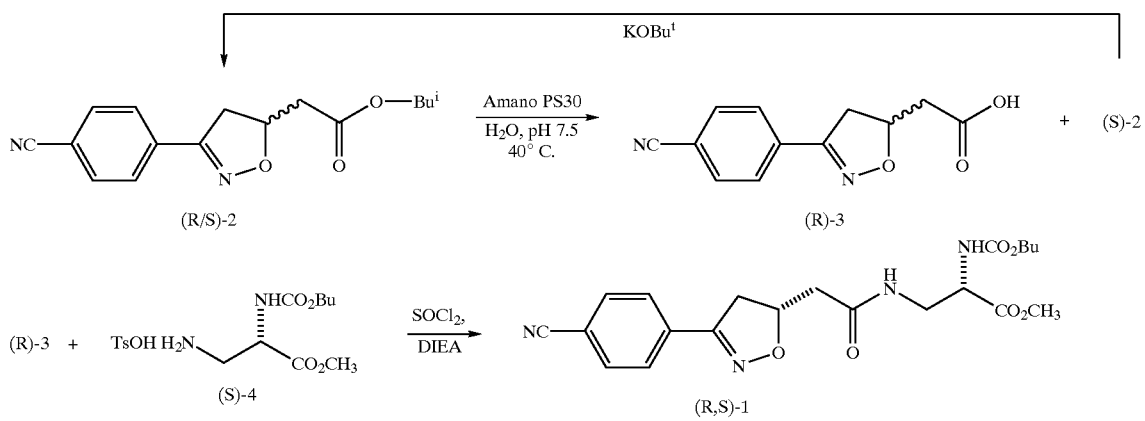

The enzyme-catalyzed enantioselective aminolysis of racemic esters to produce chiral amides is well-known (Gotor, *Bioorg. Med. Chem.* 7:2189–2197 (1999)). Aminolysis of rac-2-methyloctanoate by (R)-1-phenylethylamine in the presence of *Candida antartica* lipase (Novozym 435) produced (R)-2-methyloctanoic (R)-1-phenylethylamide in 30–40% diastereomeric excess (de) at approximately 100% conversion (Vorde et al., *Tetrahedron: Asymmetry* 7:1507–1513 (1996)). Resolution of chiral amines by reaction with an iso-alkyl ester in the presence of an enantioselective lipase such as 1*Candida antartica* lipase produced a chiral amide in high enantiomeric excess (WO 99/31264). A systematic study of the enzymatic aminolysis of racemic 2-methyl butyrate by benzylamine found that the lipases from *Rhizopus niveus, Candida antartica* B and porcine pancreas were highly enantioselective (84%–87% ee), while *Candida rugosa* and *Pseudomonas cepacia* lipases were neither highly active nor enantioselective (15% ee and 12% ee, respectively) (de Castro et al., *Tetrahedron* 54:2877–2892 (1998)). *Candida antartica* lipase catalyzed the enantioselective aminolysis of racemic 3-hydroxyesters (Garcia et al., *Tetrahedron: Asymmetry* 4:2199–2210 (1993)) or racemic 2-alkylesters or 2-haloesters (Quiros et al., *Tetrahedron: Asymmetry* 4:1105–1112 (1993)) by aliphatic amines, and the degree of enantioselectivity was dependent on the substrate and nucleophile. For the enzymatic aminolysis of dimethyl 3-hydroxyglutarate by aliphatic and aromatic amines, *Candida antartica* lipase yielded enantipure monoamidation products with very high yield, while no amidation products were observed in the presence of lipases from *Candida cylindracea* and *Pseudomonas cepacia* under identical reaction conditions (Puertas et al., *J. Org Chem.* 61:6024–6027 (1996)).

In addition to lipases, other enzymes can catalyze the enantioselective aminolysis of racemic esters. In the presence of a D-aminopeptidase from *Ochrobactrum anthropi*, the stereoselective aminolysis of racemic D,L-alanine methyl ester by a variety of alkyl and benzyl amines produced the corresponding D-alanine N-alkylamide in >99% ee (Kato et al., *Tetrahedron* 45:5743–5754 (1989)). Thiolsubtilisin catalyzed the quantitative aminolysis of Z-L-phenylalanine p-chorophenyl ester by glycinamide to produce Z-L-Phe-Gly-$NH_2$, but no reaction was observed with Z-D-phenylalanine p-chorophenyl ester (Nakatsuka et al., *J. Am. Chem. Soc.* 109:3808–3010 (1987)). Papain catalyzed the aminolysis of Bz-L-Ala-OMe by L-Val-$NH_2$ to produce Bz-L-Ala-L-Val-$NH_2$, but no reaction was observed with Bz-D-Ala-OMe (Mitin et al., *Int. J. Peptide Protein Res.* 23:528–534 (1984)).

Many additional examples exist which demonstrate that achieving a highly-enantioselective enzymatic aminolysis of a racemic ester depends on not only the choice of enzyme, but also on the chemical structure of the ester and the amine. The optimal choice of enzyme and substrate is therefore not easily predicted, but most often must be determined by a careful screening of a variety of enzymes while varying the chemical structure of potential substrates.

The problem to be solved, therefore, is to provide a facile, reliable method for the production (R)-methyl-3-[[[3-(4-cyanophenyl)-4,5-dihydro-5-isoxazolyl]acetyl]amino]-N-(butoxycarbonyl)-L-alanine ((R,S)-1) in high diasteriomeric excess.

SUMMARY OF THE INVENTION

The instant invention relates to a process for the enantioselective enzymatic aminolysis of racemic 2-[3-(4-cyanophenyl)-4,5-dihydro-5-isoxazolyl]acetate ((RIS)-I) by methyl $N_\alpha$-Boc-L-$\alpha,\beta$-diaminoproprionate.p-toluenesulfonic acid (S-4) to produce (R)-methyl-3-[[[3-(4-cyanophenyl)-4,5-dihydro-5-isoxazolyl]acetyl]amino]-N-(butoxycarbonyl)-L-alanine ((R,S)-1). More specifically, this invention pertains to a process for the enantioselective enzymatic aminolysis of racemic isobutyl 2-[3-(4-cyanophenyl)-4,5-dihydro-5-isoxazolyl]-acetate (R/S)-2 by (S)-4 to produce (R,S)-1, which is useful in the preparation of the isoxazoline-based platelet glycoprotein IIb/IIIa antagonist roxifiban.

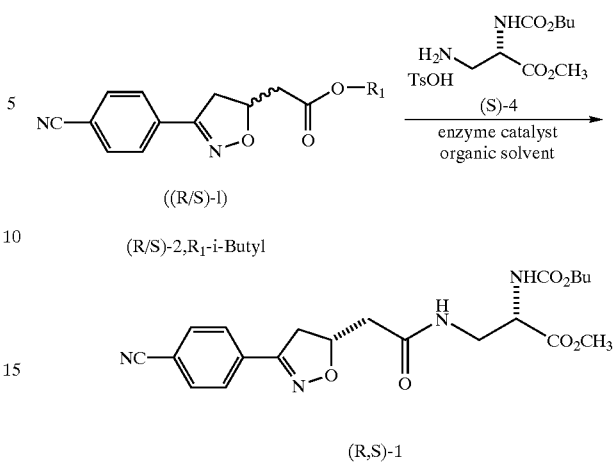

DETAILED DESCRIPTION OF THE INVENTION

Applicants have solved the stated problem with the disclosed method and reaction conditions that produce (R,S)-1 with a diasteriomeric excess as high as 92%. The instant invention is an alternative method for preparing (R,S)-1, where the direct, enzyme-catalyzed aminolysis of racemic 2-[3-(4-cyanophenyl)-4,5-dihydro-5-isoxazolyl]-acetate ((R/S)-I) by diamine (S)-4 to directly produce (R,S)-1 with high diastereoselectivity has been achieved.

Relative to previously known methods to prepare (R,S)-1, the claimed invention reduces the number of process steps to prepare (R,S)-1, generates less waste, and permits facile product recovery. The process eliminates one of two reaction steps and several costly reagents from the previous method of preparation. For example, when isobutyl 2-[3-(4-cyanophenyl)-4,5-dihydro-5-isoxazolyl]acetate (R/S)-2 is used as the ester in the enzyme-catalyzed aminolyis reactions (Scheme 2), the desired product (R,S)-1 has been prepared with a diasteriomeric excess as high as 92%.

Scheme 2

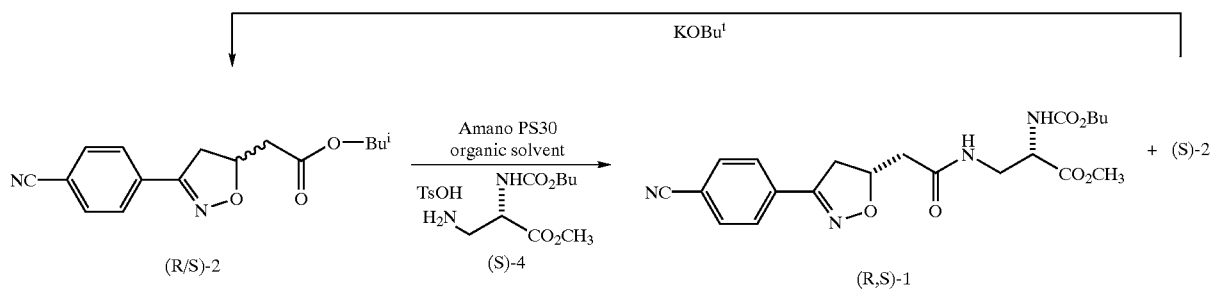

[1] Thus in one embodiment, the present invention provides for a novel process for the enantioselective enzymatic aminolysis of racemic 2-[3-(4-cyanophenyl)-4,5-dihydro-5-isoxazolyl]acetate ((R/S)-I),

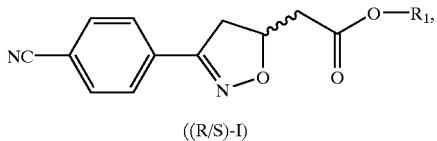

((R/S)-I)

wherein $R_1$ is selected from the group comprising of unsubstituted or substituted $C_1$–$C_6$ alkyl or alkenyl, $C_3$–$C_6$ cycloalkyl, substituted or unsubstituted aryl, substituted or unsubstituted arylalkyl, or substituted or unsubstituted heteroaryl alkyl,
by methyl $N_\alpha$-Boc-L-α,β-diaminoproprionate.p-toluene-sulfonic acid, (S)-4,

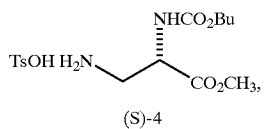

(S)-4 to produce (R)-methyl-3-[[[3-(4-cyanophenyl)-4,5-dihydro-5-isoxazolyl]acetyl]amino]-N-(butoxycarbonyl)-L-alanine, ((R,S)-1),

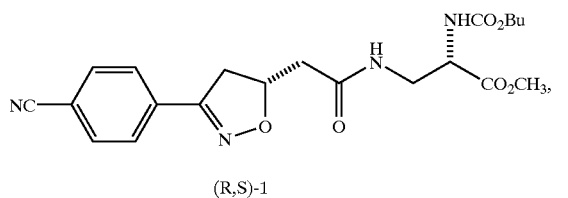

(R,S)-1 comprising:
(a) contacting racemic ((R/S)-I) with a compound of formula (S)-4, an effective amount of enzyme catalyst which is optionally immobilized on an insoluble organic or inorganic carrier, an organic solvent, and optionally a desiccant, in a reaction mixture to form a compound of formula (R,S)-1; and
(b) isolating the compound of formula (R,S)-1 from the reaction mixture of step (a).

[2] In another embodiment the present invention provides for a novel process the enantioselective enzymatic aminolysis of racemic 2-[3-(4-cyanophenyl)-4,5-dihydro-5-isoxazolyl]acetate ((R/S)-I) by methyl $N_\alpha$-Boc-L-αβ-diaminoproprionate.p-toluene-sulfonic acid, (S)-4, to produce (R)-methyl-3-[[[3-(4-cyanophenyl)-4,5-dihydro-5-isoxazolyl]acetyl]amino]-N-(butoxycarbonyl)-L-alanine ((R,S)-1), wherein the enzyme catalyst is selected from the group comprising of *Pseudomonas cepacia* lipase and *Candida antartica* lipase fraction B.

[3] In another embodiment the present invention provides for a novel process of the enantioselective enzymatic aminolysis of racemic 2-[3-(4-cyanophenyl)-4,5-dihydro-5-isoxazolyl]acetate ((R/S)-I) by methyl $N_\alpha$-Boc-L-αβ-diaminoproprionate.p-toluene-sulfonic acid, (S)-4, to produce (R)-methyl-3-[[[3-(4-cyanophenyl)-4,5-dihydro-5-isoxazolyl]acetyl]amino]-N-(butoxycarbonyl)-L-alanine, ((R,S)-1), wherein the enzyme catalyst has an adjusted pH of from about 7.0 to about 10.0.

[4] In another embodiment the present invention provides for a novel process of the enantioselective enzymatic aminolysis of racemic 2-[3-(4-cyanophenyl)-4,5-dihydro-5-isoxazolyl]acetate ((R/S)-I) by methyl $N_\alpha$-Boc-L-αβ-diaminoproprionate.p-toluene-sulfonic acid, (S)-4, to produce (R)-methyl-3-[[[3-(4-cyanophenyl)-4,5-dihydro-5-isoxazolyl]acetyl]amino]-N-(butoxycarbonyl)-L-alanine, ((R,S)-1), wherein the desiccant comprises of activated 3 Å molecular sieves or activated 4 Å molecular sieves.

[5] In another embodiment the present invention provides for a novel process of the enantioselective enzymatic aminolysis of racemic 2-[3-(4-cyanophenyl)-4,5-dihydro-5-isoxazolyl]acetate ((R/S)-I) by methyl $N_\alpha$-Boc-L-αβ-diaminoproprionate.p-toluene-sulfonic acid, (S)-4, to produce (R)-methyl-3-[[[3-(4-cyanophenyl)-4,5-dihydro-5-isoxazolyl]acetyl]amino]-N-(butoxycarbonyl)-L-alanine, ((R,S)-1), wherein the organic solvent is selected from the group comprising of methyl-t-butyl ether, diisopropyl ether, heptane, toluene, 1,4-dioxane, and acetonitrile.

[6] In another embodiment the present invention provides for a novel process of the enantioselective enzymatic aminolysis of racemic 2-[3-(4-cyanophenyl)-4,5-dihydro-5-isoxazolyl]acetate ((R/S)-I) by methyl $N_\alpha$-Boc-L-αβ-diaminoproprionate.p-toluene-sulfonic acid, (S)-4, to produce (R)-methyl-3-[[[3-(4-cyanophenyl)-4,5-dihydro-5-isoxazolyl]acetyl]amino]-N-(butoxycarbonyl)-L-alanine, ((R,S)-1), wherein the temperature of the reaction mixture is from about 0° C. to about 60° C.

[10] In another embodiment, the present invention provides for a novel process for the enantioselective enzymatic aminolysis of racemic 2-[3-(4-cyanophenyl)-4,5-dihydro-5-isoxazolyl]acetate ((RIS)-I),

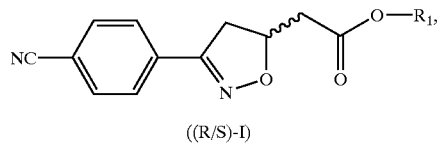

((R/S)-I)

wherein $R_1$ is selected from the group comprising of unsubstituted or substituted $C_1$–$C_6$ alkyl or alkenyl, $C_3$–$C_6$ cycloalkyl, substituted or unsubstituted aryl, substituted or unsubstituted arylalkyl, or substituted or unsubstituted heteroaryl alkyl,
by methyl $N_\alpha$-Boc-L-αβ-diaminoproprionate.p-toluene-sulfonic acid, (S)-4,

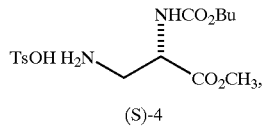

(S)-4 to produce (R)-methyl-3-[[[3-(4-cyanophenyl)-4,5-dihydro-5-isoxazolyl]acetyl]amino]-N-(butoxycarbonyl)-L-alanine, ((R,S)-1),

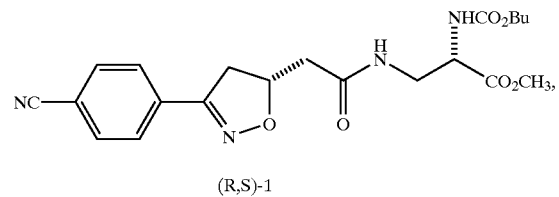

(R,S)-1 further comprising:
(a) contacting racemic ((R/S)-I) with a compound of formula (S)-4, an effective amount of enzyme catalyst which is optionally immobilized on an insoluble organic or inorganic carrier, an organic solvent, and optionally a desiccant, in a reaction mixture to form a compound of formula (R,S)-1; and (b) isolating the compound of formula (R,S)-1 from the reaction mixture of step (a);

(c) isolating unreacted S-enantiomer ((S)-I)

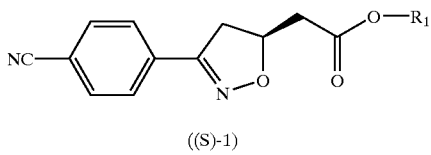

((S)-1)

from the reaction mixture of step(b);

(d) heating the unreacted S-enantiomer ((S)-I) obtained from step (c) in toluene in the presence of a catalytic amount of potassium tert-butoxide to yield racemic 2-[3-(4-cyanophenyl)-4,5-dihydro-5-isoxazolyl]-acetate ((R/S)-I); and (e) recycling the racemic 2-[3-(4-cyanophenyl)-4,5-dihydro-5-isoxazolyl]acetate ((R/S)-I) obtained from step (d) by applying steps (a) to (e); the recycling step (e) is performed from 1 to 5 times.

[14] In another embodiment, the present invention provides for a novel process for the preparation of (R)-methyl-3-[[[3-[4-(aminoiminomethyl) phenyl]-4,5-dihydro-5-isoxazolyl]acetyl]amino]-N-(butoxycarbonyl)-L-alanine monoacetate (roxifiban)

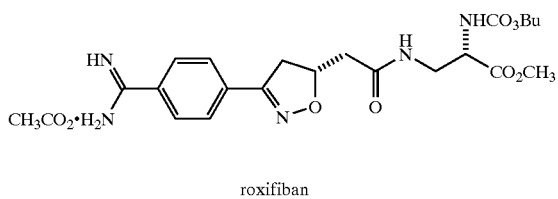

roxifiban comprising:

(a) contacting racemic 2-[3-(4-cyanophenyl)-4,5-dihydro-5-isoxazolyl]acetate ((R/S)-I)

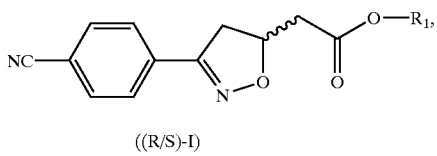

((R/S)-I)

wherein $R_1$ is selected from the group comprising of unsubstituted or substituted $C_1$–$C_6$ alkyl or alkenyl, $C_3$–$C_6$ cycloalkyl, substituted or unsubstituted aryl, substituted or unsubstituted arylalkyl, or substituted or unsubstituted heteroaryl alkyl, with methyl $N_\alpha$-Boc-L-$\alpha\beta$-diaminoproprionate.p-toluene-sulfonic acid, (S)-4,

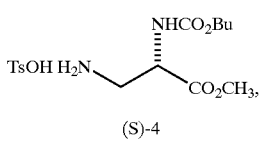

(S)-4 which is optionally immobilized on an insoluble organic or inorganic carrier, an organic solvent, and optionally a desiccant, in a reaction mixture to form a compound of formula(R,S)-1, (R)-methyl-3-[[[3-(4-cyanophenyl)-4,5-dihydro-5-isoxazolyl]acetyl]amino]-N-(butoxycarbonyl)-L-alanine,

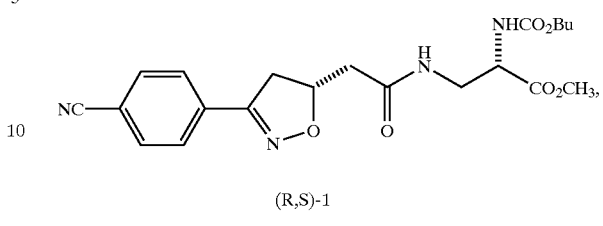

(R,S)-1

(b) isolating the compound of formula (R,S)-1 from the reaction mixture of step (a).

(c1) contacting the compound of formula (R,S)-1, isolated in step (b) with HCl and methanol in methyl acetate to form an imidate compound,

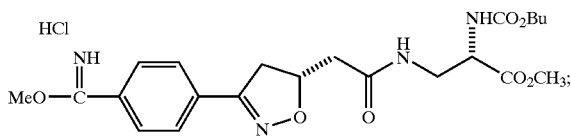

(d1) contacting the imidate compound produced in step (c1) with ammonium acetate to produce (R)-methyl-3-[[[3-[4-(aminoiminomethyl)phenyl]-4,5-dihydro-5-isoxazolyl]acetyl]amino]-N-(butoxycarbonyl)-L-alanine monoacetate; and (e1) recovering the product of step (d1).

The present invention encompasses all the different combinations or sub-combinations of the above embodiments which provide for a novel process of the enantioselective enzymatic aminolysis of racemic 2-[3-(4-cyanophenyl)-4,5-dihydro-5-isoxazolyl]acetate ((R/S)-I) by methyl $N_\alpha$-Boc-L-$\alpha\beta$-diaminoproprionate.p-toluene-sulfonic acid, (S)-4, to produce (R)-methyl-3-[[[3-(4-cyanophenyl)-4,5-dihydro-5-isoxazolyl]acetyl]amino]-N-(butoxycarbonyl)-L-alanine, ((R,S)-1).

In this disclosure, a number of terms and abbreviations are used. The following definitions are provided.

The meaning of abbreviations is as follows: "sec" means second(s), "min" means minute(s), "h" means hour(s), "d" means day(s), "µL" means microliter(s), "mL" means milliliter(s), "L" means liters, "mm" means millimolar, "M" means molar, "mmol" means millimole(s).

"(R)-Methyl-3-[[[3-[4-(aminoiminomethyl)phenyl]-4,5-dihydro-5-isoxazolyl]acetyl]amino]-N-(butoxycarbonyl)-L-alanine monoacetate" is abbreviated as roxifiban.

"(R)-Methyl-3-[[[3-(4-cyanophenyl)-4,5-dihydro-5-isoxazolyl]acetyl]amino]-N-(butoxycarbonyl)-L-alanine" is abbreviated as (R,S)-1.

"Racemic isobutyl 2-[3-(4-cyanophenyl)-4,5-dihydro-5-isoxazolyl]acetate " is abbreviated as (R/S)-2.

"(R)-2-[3-(4-cyanophenyl)-4,5-dihydro-5-isoxazolyl] acetic acid" is abbreviated as (R)-3.

"Methyl $N_\alpha$-Boc-L-$\alpha\beta$-diaminoproprionate.p-toluene-sulfonic acid" is abbreviated as (S)-4.

"*Pseudomonas cepacia* lipase" is abbreviated PS30 lipase.

"*Candida antartica* lipase fraction B" is abbreviated as CAL B.

"*Candida antartica* lipase fraction A" is abbreviated as CAL A.

As used herein, "contacting" is intended to represent bringing the reactants together in an appropriate medium such to allow the chemical reaction to take place.

As used herein, "cycloalkyl" is intended to include saturated ring groups, including mono-, bi-, or poly-cyclic ring systems, such as cyclopropyl, cyclobutyl, cyclopentyl, cyclohexyl, cycloheptyl, cyclooctyl, and adamantyl.

"Aryl" is intended to mean phenyl or naphthyl. The term "arylalkyl" represents an aryl group attached through an alkyl bridge; for example aryl($C_1$–$C_2$)alkyl is intended to mean benzyl, phenylethyl and the like.

As used herein, "alkyl" is intended to include both branched and straight-chain saturated aliphatic hydrocarbon groups having the specified number of carbon atoms; for example, $C_1$–$C_4$ alkyl includes methyl, ethyl, n-propyl, i-propyl, n-butyl, i-butyl, s-butyl, and t-butyl; for example $C_1$–$C_{10}$ alkyl includes $C_1$–$C_4$ alkyl, pentyl, hexyl, heptyl, octyl, nonyl, decyl, and isomer thereof.

As used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl. The term heteroaryl alkyl represents an heteroaryl group attached through an alkyl bridge; for example heteroaryl ($C_1$–$C_2$) alkyl is intended to mean pyridyl methyl, furanyl ethyl, and the like.

As used herein, any carbon range such as "$C_x$–$C_y$" is intended to mean a minimum of "x" carbons and a maximum of "y" carbons representing the total number of carbons in the substituent to which it refers. For example, "$C_3$–$C_{10}$ alkylcarbonyloxyalkyl" could contain one carbon for "alkyl", one carbon for "carbonyloxy" and one carbon for "alkyl" giving a total of three carbons, or a larger number of carbons for each alkyl group not to exceed a total of ten carbons.

"Alkenyl" is intended to include hydrocarbon chains of either a straight or branched configuration and one or more unsaturated carbon—carbon bonds which may occur in any stable point along the chain, such as ethenyl, 1-propenyl, 2-propenyl, 1-butenyl, 2-butenyl, 3-butenyl, 1,3-butadienyl and the like.

The term "substituted" means that one or more hydrogens on the molecule or atom are replaced with 1, 2, 3, 4, 5, or 6 substitution groups provided that the indicated atom's normal valency is not exceeded, and that the substitution results in a stable compound. Such "substitution groups" may be selected from the group consisting of H, —O—$C_1$–$C_4$ alkyl, $C_1$–$C_6$ alkenyl, $C_3$–$C_6$ cycloalkyl, arylalkyl, heteroaryl, F, Cl, Br, I, —CN, —$NO_2$, or $CF_3$.

As used herein, "enzyme catalyst" is intended to include an enzyme which facilitates the production one of two diastereomers with a high degree of enantioselectivity at ca. 50% conversion of a racemic mixture, such as *Pseudomonas cepacia* lipase and *Candida antartica* lipase fraction B, in the enantioselective aminolysis of racemic 2-[3-(4-cyanophenyl)-4,5-dihydro-5-isoxazolyl]acetate ((R/S)-I) by methyl $N_\alpha$-Boc-L-$\alpha\beta$-diaminoproprionate.p-toluenesulfonic acid, (S)-4, to produce (R)-methyl-3-[[[3-(4-cyanophenyl)-4,5-dihydro-5-isoxazolyl]acetyl]amino]-N-(butoxycarbonyl)-L-alanine, ((R,S)-1).

As used herein, "an effective amount of enzyme catalyst" typically ranges from 0.1 mg to 50 mg per mL of total reaction volume, preferably from 1 mg to 20 mg per mL of total reaction volume for unimmobilized enzyme, and typically ranges from 0.1 mg to 1.0 g of immobilized enzyme per mL of reaction mixture, preferably from 1 mg to 200 mg of immobilized enzyme per mL of reaction mixture.

As used herein, "desiccant" is intended to include any material which will absorb water without interfering with the enzyme catalyzed reaction, such as molecular sieves or sodium sulfate.

As used herein, an enzyme catalyst having "an adjusted pH of A" is intended to mean that an enzyme catalyst is first added to a 0.10 M phosphate buffer, at a concentration of about 30 mg of enzyme catayst/mL of buffer solution, then the buffer solution is adjusted to pH A. Subsequent lyophilizing the enzyme solution provides an enzyme catalyst which has an adjusted pH A.

As used herein, "immobilization" of an enzyme include, but is not limited to, the fixation by adsorption or attachment, of an enzyme to porous or non porous insoluble inorganic carriers and porous or non porous insoluble organic carriers.

As used herein, an "insoluble organic carrier" is a support which an enzyme is absorbed or attached to such as, but is not limited to, polyethylene or polypropylene beads, ion exchange resins, alginate, carrageenan, polyvinyl-alcohol, or polyacylamide gel.

As used herein, an "insoluble inorganic carrier" is a support which an enzyme is absorbed or attached to such as, but is not limited to, diatomaceous earth (celite), silica, porous glass beads, alumina, zirconia, titania and the like.

As used herein, an "organic solvent" is a non-aqueous containing organic solvent which includes by way of example and without limitation, hydrocarbon solvents such as benzene, cyclohexane, pentane, hexane, toluene, cycloheptane, methylcyclohexane, heptane, ethylbenzene, m-, o-, or p-xylene, octane, indane, or nonane; ether solvents such as dimethoxymethane, tetrahydrofuran, 1,3-dioxane, 1,4-dioxane, tetrahydrofuran, diethyl ether, ethylene glycol dimethyl ether, ethylene glycol diethyl ether, diethylene glycol dimethyl ether, diethylene glycol diethyl ether, triethylene glycol, dimethyl ether, anisole, or t-butyl methyl ether; and aprotic solvent such as acetonitrile or propionitrile.

"Diisopropyl ether" is abbreviated DIPE.

"Methy-t-butyl ether" is abbreviated MTBE.

The term "aminolysis" refers to the addition of an amine to an ester to produce an amide and the corresponding alcohol.

The term "((R/S)-I)" is defined as a racemic mixture of compounds ((R)-I) and ((S)-I), wherein the chiral carbon of ((R)-I) has an (R) absolute configuration, and chiral carbon of ((S)-I) has an (S) absolute configuration.

The term "enantiomer" describes one of a pair of molecular entities which are mirror images of each other and non-superimposable.

The term "diasteriomer" describes stereoisomers not related as mirror images. Diasteriomers are characterized by differences in physical properties and by some differences in chemical behavior towards achiral as well as chiral reagents.

The term "enantiomeric excess" is defined for a mixture of (+)- and (−)-enantiomers, with composition given as the mole or weight fraction $F_{(+)}$ and $F_{(-)}$ (where the sum of $F_{(+)}$ and $F_{(-)}$=1), the enantiomeric excess is defined as $|F_{(+)}-F_{(-)}|$, and the percent enantiomeric excess by $100|F_{(+)}-F_{(-)}|$. "Enantiomeric excess" is abbreviated as ee.

The term "diastereomeric excess" is defined by analogy with enantiomeric excess, as $D_1$–$D_2$ (and the percent diastereomeric excess as $100(D_1-D_2)$), where the mole fractions of two diasteriomers in a mixture of the fractional yields of two diastereomers formed in a reaction are $D_1$ and $D_2$ (where the sum of $D_1$ and $D_2=1$). The term is not applicable when more than two diastereomers are present. "Diasteriomeric excess" is abbreviated as de.

The term "enantioselectivity" or the symbol "E" refers to the selective capacity of an enzyme to generate (from a racemic substrate) one enantiomer relative to the other in a product racemic mixture. The enantioselectivity resides in a difference in conversion rates between the enantiomers in question. Reaction products are obtained that are enriched in one of the enantiomers (or in the instant invention, where aminolysis by a chiral amine occurs, the mixture of reaction products is enriched in one of the diastereomers). For practical purposes, it generally is desirable for one of the enantiomers to be obtained in large excess. This result is achieved by terminating the conversion at a certain degree of conversion. The enantioselectivity is quantitatively expressed by the following formula (U.S. Pat. No. 5,541,080; Chen et al., *J. Am. Chem. Soc.* 104:7294–7299 (1982)):

$$\frac{\ln[1 - c(1 + ee(P))]}{\ln[1 - c(1 - ee(P))]} = E$$

$$c = 1 - \frac{A + B}{A_0 + B_0} \quad ee(P) = \frac{P - Q}{P + Q}$$

wherein:

c is the extent of substrate conversion for the enzyme catalyzed product, ee(P) is the enantiomeric excess of the product fraction, A and B are the fast- and slow-reacting enantiomers, and P and Q are the fast- and slow-reaction product enantiomers (or in the present case, diastereomers). The general theory regarding enantioselective conversion described in these publications also applies to the present process.

Several potential by-product-forming reactions would result in yield loss or a decrease in diastereomeric excess (de) of (R,S)-1, which has two chiral centers (Scheme 3). Potential by-product-forming reactions include the following: a) non-enzymatic amination of (R/S)-2 by (S)-4, b) enzymatic hydrolysis of (R/S)-2 to (R)-3 (if water is present in the organic solvent), c) enzymatic hydrolysis of the product (R,S)-1 (if water is present in the organic solvent), d) enzyme-catalyzed aminolysis of (S)-4 by an additional equivalent of (S)-4, or e) enzymatic or non-enzymatic amination of the product (R,S)-1 to produce an aminated by-product.

The reaction is run in a non-aqueous solvent to prevent enzymatic hydrolysis of (R/S)-2. The free amine of (S)-4 is unstable, and was found to polymerize in aqueous or organic solvents. The tosylate salt (S)-4 is stable in organic solvents, but it was not certain that (S)-4 could react with the enzyme-acyl intermediate generated by the reaction of (R/S)-2 with the enzyme. It was first demonstrated that, in the presence or absence of *Pseudomonas cepacia* (formerly *Pseudomonas sp.*) (Amano PS30) lipase or *Candida antartica* lipase B (CAL B), there was no significant change in concentration of (S)-4 in diisopropyl ether (DIPE), methyt-butyl ether (MTBE), heptane, or toluene after 24 h at 25° C. In aqueous 0.4 M phosphate buffer (pH 8.0), a significant (>75%) loss of (S)-4 was observed after 24 h at 25° C.

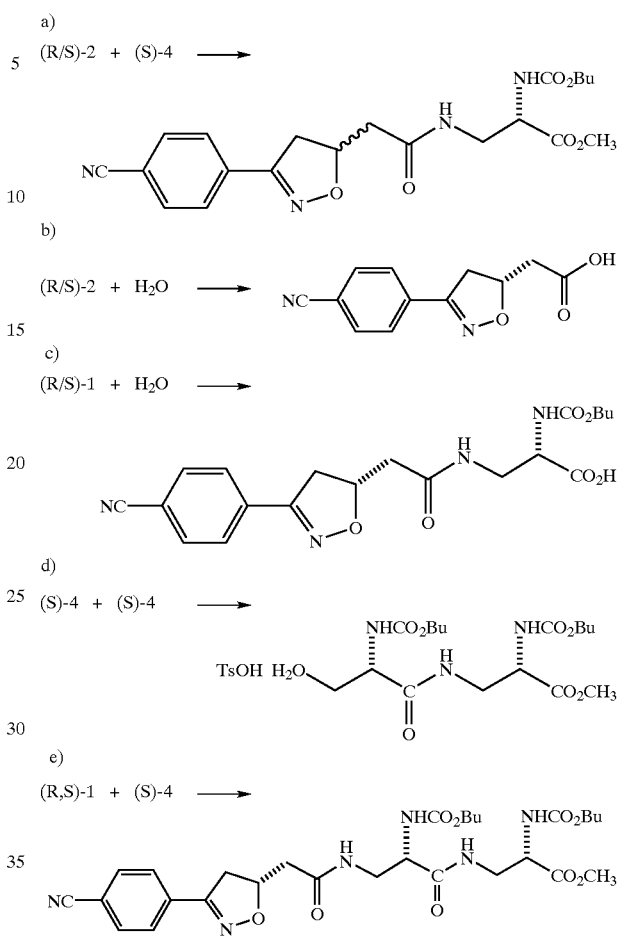

Scheme 3

Having demonstrated that (S)-4 was stable in non-aqueous reaction mixtures, aminolysis reactions were run by first adjusting the pH of a 30 mg/mL solution or suspension of an enzyme catalyst, including but not limited to PS30 lipase and CAL B, in 0.10 M phosphate buffer to pH 8.0, then lyophilizing the enzyme solution to obtain a "dry" enzyme preparation. This catalyst was subsequently used in reactions containing 52 mM (R/S)-2 and from 37.5 to 100 mM (S)-4 in DIPE, MTBE, heptane, toluene, or acetonitrile, at temperatures of from 24° C. to 40° C. Product mixtures initially contained significant amounts of the ester hydrolysis product (R)-3 as the sole reaction by-product, indicating that a significant amount of water was available in the reaction mixtures, possibly coming from the organic solvent, enzyme preparation, or starting materials. None of the other potential reaction by-products depicted in Scheme 3 were observed in significant amounts (<1%). Drying the reaction solvents over desiccants such as activated 3 Å or 4 Å molecular sieves prior to use improved selectivity to (R,S)-1 over (R)-3, and inclusion of 10–35 mg/mL of powdered, activated 3 Å or 4 Å molecular sieves in the reaction mixture also further improved selectivity to (R,S)-1.

Table A lists the selectivities to (R,S)-1 (versus hydrolysis, the only by-product-forming reaction observed), and the corresponding de of (R,S)-1 over a conversion range of from approximately 20%–50%, using PS30 lipase or CAL B in DIPE, MTBE, or heptane (results summarized from Examples 2, 5, 6, and 7).

TABLE A

Enzyme-catalyzed Enantioselective Amination of (R/S)-2 by (S)-4 using PS30 Lipase or CAL B.

| solvent | Example | enzyme | (R/S)-2 conv. (%) | (R,S)-1 + (S,S)-1 sel. (%) | (R,S)-1: (S,S)-1 | (R,S)-1 de (%) |
|---|---|---|---|---|---|---|
| DIPE | 2 | PS30 | 23 | 95 | 93:7 | 86 |
| DIPE | 2 | PS30 | 44 | 92 | 87:13 | 74 |
| MTBE | 5 | PS30 | 27 | 89 | 93:7 | 86 |
| MTBE | 5 | PS30 | 46 | 88 | 89:11 | 78 |
| heptane | 6 | PS30 | 24 | 90 | 86:14 | 72 |
| MTBE | 7 | CAL B | 31 | 81 | 96:4 | 92 |

Further improvement in de may be achieved by screening additional enzymes or by using alternative organic solvents. While PS30 lipase and CAL B each produced the desired diastereomer (R,S)-1 in high de, *Candida antartica* lipase A (CAL A) produced the wrong diastereomer (i.e., (S,S)-1 instead of (R,S)-1) at an equally high de (76% de at 35% conversion of (R/S)-2; Example 8), indicating that not all enzymes capable of catalyzing the aminolysis of (R,S)-1) by (S)-4 will produce the desired diastereomer. A de for (R,S)-1 of 86% (produced by PS30 lipase) corresponds to an actual yield of the desired diastereomer of 93% (based on total (R,S)-1 and (S,S)-1 produced); the subsequent separation of these diastereomers by crystallization is readily performed, and produces the desired diastereomer in very high purity.

Enzymatic Aminolysis of Racemic (R/S-2) by (S)-4:

An enzyme catalyst for the enzymatic aminolysis of racemic (R/S-2) by (S)-4 was desired which would produce one of two diastereomers with a high degree of enantioselectivity at ca. 50% conversion of a racemic mixture. If an enzyme catalyst has a low enantioselectivity for one of the two enantiomers present, the highest diasteriomeric excesses of product obtainable is achieved by running the reaction to conversions considerably less than 50% conversion, which results in an undesirable and uneconomical yield loss. The calculations of ee and enantioselectivity (E) relative to conversion in enzymatic resolutions of racemic mixtures of chiral compounds have been described in U.S. Pat. No. 5,541,080.

A racemic mixture of (R/S)-2 was screened in the aminolysis reaction against a variety of different enzyme preparations, and both PS30 lipase and CAL B were found to catalyze the aminolysis of (R/S)-2 by (S)-4 to produce (R,S)-1 in high de at up to 50% conversion. For example, reacting racemic (R/S)-2 at a concentration of approximately 52 mM in a non-aqueous organic solvent containing approximately 38 mM (S)-4 and 30 mg/mL of PS30 lipase at 40° C. for 48 h produced a 74% de of (R,S)-1 at 44% conversion and 92% selectivity. This result corresponds to an 80% yield of (R,S)-1 based on converted (R/S)-2, and only an 8% yield of (R)-3 and a 12% yield of (S,S)-1 based on converted (R/S)-2. Further optimizing reaction conditions could lead to further improvements in selectivity and de. A check for the aminolysis of (R/S)-2 by (S)-4 without added enzyme under identical reaction conditions in MTBE, DIPE, heptane, toluene, and 1,4-dioxane demonstrated that there was no detectable conversion of (R/S)-2.

The production of (R,S)-1 and (S,S)-1 as aminolysis reaction products was confirmed by preparing authentic samples of (R,S)-1, (S,S)-1, (S,R)-1, and (R,R)-1, separating all four diastereomers by chiral HPLC, and comparing product retention times with the authentic standards. Isolating (R,S)-1 from the product mixture can be readily performed (e.g., by extraction) in high yield and purity.

All starting materials for the enzymatic aminolysis reactions were obtained from commercial sources, or prepared according to Zhang et al. (*J. Org. Chem.* 62:2466–2470 (1997)). The enzymes examined as catalysts in the present invention were obtained from Amano, Sigma, or Roche Biochemicals. Weights reported in the following Examples for soluble PS30 lipase, CAL B, CAL A, and all other enzyme preparations examined are for the crude enzyme preparations; for example, the CAL B protein was determined to be approximately 15 wt % of the total crude enzyme preparation of CHIRAZYME® L-2 from Roche Biochemicals.

*Candida antartica* lipase B (CAL B) can be isolated from *Candida antartica* cells following published procedures (Patkar et al., *Ind. J. Chem., Sect. B* 32B:76–80 (1993)) or obtained from commercial sources (e.g., SP 525 from NOVO Nordisk; CHIRAZYME® L-2 from Roche Biochemicals) and used as catalyst without any pretreatment. *Pseudomonas cepacia* lipase (PS30) was obtained from Amano. PS30 lipase or CAL B can also be immobilized in a polymer matrix, on an insoluble organic support, or on an insoluble inorganic support which simplifies catalyst recovery for reuse; these immobilization methods have been widely reported and are well-known to those skilled-in-the-art (Methods in Biotechnology, Vol. 1: Immobilization of Enzymes and Cells; Gordon F. Bickerstaff, Editor; Humana Press, Totowa, N.J., USA; 1997). Methods for immobilization of the enzyme include, but are not limited to, immobilization in insoluble organic carriers such as alginate, carrageenan, polyvinylalcohol, or polyacylamide gel, as well as immobilization by adsorption or attachment to porous or non porous insoluble organic carriers such as polyethylene or polypropylene beads, ion exchange resins, or insoluble inorganic carriers such as diatomaceous earth (celite), silica, porous glass beads, alumina, zirconia, titania and the like. Membrane separation of the soluble enzyme from the reaction mixture may also be used. Lipases with a substrate activity and enantiospecificity similar to that of PS30 lipase or CAL B can also be used in the present invention.

The amount of unimmobilized or immobilized enzyme (mg/mL) in the reaction mixture is chosen to obtain the desired rate of reaction. The weight of unimmobilized enzyme (as crude enzyme preparation, not purified protein) in the aminolysis reactions of the present invention typically ranges from 0.1 mg to 100 mg per mL of total reaction volume, preferably from 10 mg to 60 mg per mL of total reaction volume. The amount of immobilized enzyme (mg/mL) in the reaction mixture is also chosen to obtain the desired rate of reaction, and is dependent on the specific activity of the immobilized enzyme catalyst. The weight of immobilized enzyme (as crude enzyme preparation, not purified protein) in the aminolysis reactions of the present invention typically ranges from 0.1 mg to 1.0 g of immobilized enzyme per mL of reaction mixture, preferably from 1 mg to 200 mg of immobilized enzyme per mL of reaction mixture. In the case of immobilized enzymes the reaction can also be run by passing the reaction mixture containing (R/S)-2 through a column containing the immobilized enzyme.

Racemic 2-[3-(4-cyanophenyl)-4,5-dihydro-5-isoxazolyl]-acetate formula ((R/S)-I)),

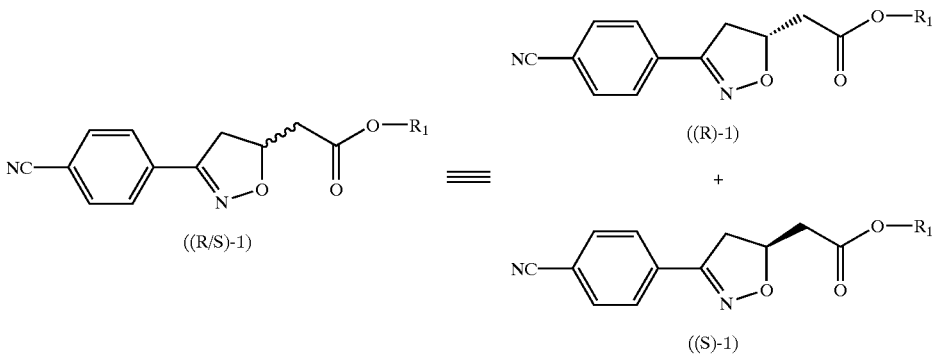

is readily prepared as described by Zhang et al., (J. Org. Chem. 62:2466–2470 (1997) where $R_1$ may be unsubstituted or substituted $C_1$–$C_6$ alkyl or alkenyl, $C_3$–$C_6$ cycloalkyl, substituted or unsubstituted aryl, substituted or unsubstituted arylalkyl, or substituted or unsubstituted heteroaryl alkyl. The preferred substrate in the present invention is racemic isobutyl 2-[3-(4-cyanophenyl)-4,5-dihydro-5-isoxazolyl] acetate (R/S)-2.

Concentrations of racemic 2-[3-(4-cyanophenyl)-4,5-dihydro-5-isoxazolyl]acetate and/or (S)-4 in reaction mixtures described by the present invention may vary, and include concentrations greater than the solubility limit of racemic 2-[3-(4-cyanophenyl)-4,5-dihydro-5-isoxazolyl] acetate ((R/S)-I) and/or (S)-4 in the reaction mixture. The solubility of the racemic 2-[3-(4-cyanophenyl-4,5-dihydro-5-isoxazolyl]acetate ((R/S)-I) and (S)-4 is dependent on several parameters, including the temperature of the reaction mixture and the salt concentration (reactants and products) in the reaction mixture. A preferred range of initial concentration of racemic 2-[3-(4-cyanophenyl)-4,5-dihydro-5-isoxazolyl]acetate ((R/S)-I) is from 50 mM to 500 mM, but higher concentrations may also be employed. A preferred range for the molar ratio of (S)-4 to racemic 2-[3-(4-cyanophenyl)-4,5-dihydro-5-isoxazolyl]acetate ((R/S)-I) is from 0.50:1 to 0.75:1, but lower or higher concentrations of (S)-4 relative to racemic 2-[3-(4-cyanophenyl)-4,5-dihydro-5-isoxazolyl]acetate ((RIS)-I) may also be employed. The aminolysis reactions are preferably performed in a reaction mixture containing, in addition to (S)-4 and racemic 2-[3-(4-cyanophenyl)-4,5-dihydro-5-isoxazolyl]acetate ((R/S)-I), (preferably (R/S)-2), the enzyme catalyst (which has been dried using methods known in the art, for example, by lyophilization or azeotropic distillation), an organic solvent selected from but not limited to the group comprising of DIPE, MTBE, heptane, toluene, 1,4-dioxane and acetonitrile (dried over activated 3 Å or 4 Å molecular sieves), and from 0–50 mg/mL of powdered, activated 3 Å or 4 Å molecular sieves. As the reaction progresses, the starting materials dissolve in the reaction mixture, and eventually complete conversion of one isomer is obtained. The reaction may be carried out in a single batch reaction or in a continuous process.

The temperature of the aminolysis reaction is chosen to optimize the reaction rate, the stability of the enzyme catalyst activity, and the stability of (S)-4, racemic 2-[3-(4-cyanophenyl)-4,5-dihydro-5-isoxazolyl]acetate ((RIS)-I) and (R,S)-1. The temperature of the reaction may range from just above the freezing point of the suspension to 600° C., with a preferred range of reaction temperature of from 15° C. to 45° C.

The pH of the enzyme preparation is chosen to optimize the reaction rate, the stability of the enzyme catalyst activity, and the stability of stability of (S)-4, racemic 2-[3-(4-cyanophenyl)-4,5-dihydro-5-isoxazolyl]acetate ((R/S)-I) and (R,S)-1. Solutions or suspensions of the enzyme catalyst were prepared in an appropriate buffer, for example, phosphate buffer (50 mM to 200 mM, preferably 100 mM), and the pH of the resulting solutions or suspensions were adjusted to a pH of from 7.0 to 10.0, preferably between a pH of from 8.0 to 8.5. The resulting enzyme preparation was then frozen and lyophilized to remove water, resulting in a dried enzyme catalyst that was used to catalyze the aminolysis of racemic 2-[3-(4-cyanophenyl)-4,5-dihydro-5-isoxazolyl]acetate ((RIS)-I) by (S)-4.

Separating (R,S)-1 from the other components of the enzyme-catalyzed aminolysis reaction may readily be accomplished, using the difference in chemical properties of (R,S)-1 relative to the remaining components. The entire reaction mixture can be diluted with an appropriate organic solvent that will dissolve unreacted (S)-2-[3-(4-cyanophenyl)-4,5-dihydro-5-isoxazolyl]acetate ((S)-I) and (R,S)-1, while leaving unreacted (S)-4 (a tosylate salt), molecular sieve, and the enzyme prepartion as undissolved solids which can be separated by filtration or centrifugation. Examples of solvents that can extract (S)-2-[3-(4-cyanophenyl)-4,5-dihydro-5-isoxazolyl]acetate ((S)-I) and (R,S)-1 from the remaining reaction components include (but are not limited to) dichloromethane, chloroform, toluene, methyl tert-butyl ether, or diisopropyl ether. The desired product (R,S)-1 and (S)-2-[3-(4-cyanophenyl)-4,5-dihydro-5-isoxazolyl]acetate ((S)-I) can then be separated by methods well-known to those skilled in the art, including column chromatography, selective precipitation, or fractional crystallization.

The unreacted (S)-2-[3-(4-cyanophenyl)-4,5-dihydro-5-isoxazolyl]acetate ((S)-I) recovered from the reaction mixture can be racemized, for example, by heating for 1 h in toluene at 40° C. in the presence of a catalytic amount of potassium tert-butoxide (Zhang et al., (1997)), and the racemate used as starting material in a subsequent enzymatic amination reaction, thereby increasing the yield of (R,S)-1 produced, and decreasing the amount of waste produced in the present invention.

The product of the present invention, (R,S)-1, may be further converted to (R)-methyl-3-[[[3-[4-(aminoiminomethyl) phenyl]-4,5-dihydro-5-isoxazolyl] acetyl]amino]-N-(butoxycarbonyl)-L-alanine monoacetate (roxifiban), according to previously-reported procedures (Zhang et al., (1997)). The isolated (R,S)-1 is first reacted with hydrochloric acid and methanol in methyl acetate to produce an imidate (see below).

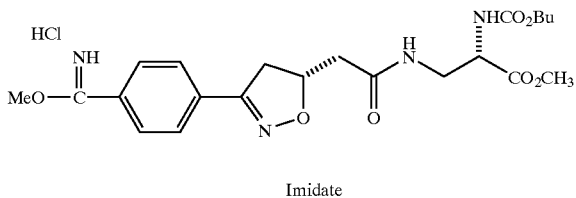

Imidate

The resulting imidate is then reacted with ammonium acetate to produce (R)-methyl-3-[[[3-[4-(aminoiminomethyl)phenyl]-4,5-dihydro-5-isoxazolyl]acetyl]amino]-N-(butoxycarbonyl)-L-alanine monoacetate.

A hydroxyamine method for further converting nitriles to the amidine roxifiban is disclosed in U.S. Pat. No. 5,962,693 (DuPont Pharmaceuticals Company, Wilmington, Del., USA).

General Methods

In the following examples, which serve to further illustrate the invention, analysis of mixtures of isobutyl (R/S)-2-[3-(4-cyanophenyl)-4,5-dihydro-5-isoxazolyl]acetate, (R/S)-methyl-3-[[[3-(4-cyanophenyl)-4,5-dihydro-5-isoxazolyl]acetyl]amino]-N-(butoxycarbonyl)-L-alanine, and (R/S)-2-[3-(4-cyanophenyl)-4,5-dihydro-5-isoxazolyl] acetic acid were performed by HPLC using the following method with UV detection at 260 nm:

column: Eclipse XDB-C8, 4.6×250 mm
temperature: 40° C.
flow rate: 1.0 mL/min
mobil phase A: 0.1% trifluoroacetic acid/0.1% triethylamine in d.d. $H_2O$
mobil phase B: 0.1% trifluoroacetic acid in THF (unstabilized)

| gradient: | t = 0 min | 85% A, 15% B |
|---|---|---|
| | t = 10 min | 85% A, 15% B |
| | t = 32 min | 50% A, 50% B |
| | t = 40 min | 50% A, 50% B |
| | t = 42 min | 85% A, 15% B |
| | t = 52 min | 85% A, 15% B |

Chiral HPLC analysis of (R)- and (S)-isobutyl 2-[3-(4-cyanophenyl)-4,5-dihydro-5-isoxazolyl]acetate and (R)- and (S)-2-[3-(4-cyanophenyl)-4,5-dihydro-5-isoxazolyl] acetic acid was performed using the following method with UV detection at 280 nm:

Column: Daicel Chiralcel OJ, 4.6×250 mm
Temperature: 38° C.
Flow rate: 0.90 mL/min
Mobil phase: 0.25% trifluoroacetic acid in 81% hexane/ 19% ethanol Chiral HPLC analysis of (R)- and (S)-methyl-3-[[[3-(4-cyanophenyl)-4,5-dihydro-5-isoxazolyl]acetyl]amino]-N-(butoxycarbonyl)-L-alanine, as well as standards (R)- and (S)-methyl-3-[[[3-(4-cyanophenyl)-4,5-dihydro-5-isoxazolyl]acetyl]amino]-N-(butoxycarbonyl)-D-alanine, was performed using the following method with UV detection at 280 nm:

column: two Daicel Chiralcel OJ, 4.6×250 mm, in series
temperature: 40° C.
flow rate: 0.75 mL/min
mobil phase: 80% heptane, 20% ethanol

EXAMPLE 1

*Pseudomonas cepacia* Lipase-Catalyzed Aminolysis of Racemic Isobutyl 2-[3-(4-Cyanophenyl)-4,5-Dihydro-5-Isoxazolyl]Acetate Into a series of 4-mL glass vials was added *Pseudomonas cepacia* lipase (Amano PS30 lipase, 30 mg) and 1.0 mL of 100 mM $NaH_2PO_4$ (pH 8.0, adjusted with 50% aqueous NaOH), and the resulting solution was frozen and lyophilized. To each vial was then added of 15 mg of methyl $N_\alpha$-Boc-L-$\alpha\beta$-diaminoproprionate.p-toluenesulfonic acid ((S)-4) (38.3 mM), 15 mg of racemic isobutyl 2-[3-(4-cyanophenyl)-4,5-dihydro-5-isoxazolyl]acetate ((R,S)-2) (52.3 mM), 10–20 mg of powdered, activated 3 Å molecular sieves, 1.0 mL of diisopropyl ether (dried over activated 3 Å molecular sieves), and a magnetic stir bar. The vials were capped and the reaction mixtures stirred at 24° C. for 48 h.

After the desired reaction time, the individual reactions were prepared for analysis by cooling the product mixtures to 25° C and then evaporating the solvent by flowing a stream of dry nitrogen over the product mixture. The resulting solid was mixed with a) 18.0 mL of a 1:1 (v/v) mixture of tetrahydrofuran and 0.1% (v/v) acetic acid in distilled, deionized water (adjusted to pH 2.0 with 6.0 N HCl), b) 2.0 mL of 30 mM p-toluamide (HPLC external standard) in a 1:1 (v/v) mixture of tetrahydrofuran and 0.1% (v/v) acetic acid in distilled, deionized water (adjusted to pH 2.0 with 6.0 N HCl), and c) 0.108 mL of 6N HCl. A 1-mL sample of the resulting mixture was centrifuged to remove undissolved solids, and the supernatant analyzed for (R/S)-isobutyl 2-[3-(4-cyanophenyl)-4,5-dihydro-5-isoxazolyl]acetate ((R/S)-2), (R/S)-methyl-3-[[[3-(4-cyanophenyl)-4,5-dihydro-5-isoxazolyl]acetyl]amino]-N-(butoxycarbonyl)-L-alanine ((R,S)-1) and (R/S)-2-[3-(4-cyanophenyl)-4,5-dihydro-5-isoxazolyl]acetic acid (ester hydrolysis product) by HPLC.

A second 2.0 mL sample was evaporated to dryness under vacuum, then 1 mL of ethanol was added to the resulting solid and the suspension heated at 50° C. for 1.0 min. The resulting suspension was filtered (0.45 μm) and analyzed by chiral HPLC for (R)- and (S)-isobutyl 2-[3-(4-cyanophenyl)-4,5-dihydro-5-isoxazolyl]acetate, (R)- and (S)-methyl-3-[[[3-(4-cyanophenyl)-4,5-dihydro-5-isoxazolyl]acetyl]amino]-N-(butoxycarbonyl)-L-alanine and (R)- and (S)-2-[3-(4-cyanophenyl)-4,5-dihydro-5-isoxazolyl]acetic acid. The results are summarized in Table 1.1.

TABLE 1.1

Enantioselective Amination of (R/S)-2 at 24° C. using *Pseudomonas cepacia* Lipase

| time (h) | 3Å sieves (mg/mL) | (R/S)-2 conv. (%) | (R/S)-1 + (S,S)-1 sel. (%) | (R,S)-1: (S,S)-1 | (R,S)-1 de (%) |
|---|---|---|---|---|---|
| 48 | 20 | 15 | 96 | 88:12 | 76 |
| 48 | 15 | 18 | 96 | 89:11 | 78 |
| 48 | 10 | 34 | 96 | 87:13 | 74 |

EXAMPLE 2

*Pseudomonas cepacia* Lipase-Catalyzed Aminolysis of Racemic Isobutyl 2-[3-(4-Cyanophenyl)-4,5-Dihydro-5-Isoxazolyl]Acetate The procedure in Example 1 was repeated, except that 20 g/mL of 3 Å powdered, activated molecular sieves were used in all reactions, and the reaction temperature was 40° C. The results are summarized in Table 2.1.

TABLE 2.1

Enantioselective Amination of (R/S)-2 using *Pseudomonas cepacia* Lipase

| time (h) | temp. (° C.) | (R/S)-2 conv. (%) | (R,S)-1 + (S,S)-1 sel. (%) | (R,S)-1: (S,S)-1 | (R,S)-1 de (%) |
|---|---|---|---|---|---|
| 24 | 40 | 16 | 89 | 96:4 | 92 |
| 24 | 40 | 23 | 95 | 93:7 | 86 |
| 24 | 40 | 25 | 93 | 92:8 | 84 |
| 24 | 40 | 28 | 98 | 91:9 | 82 |
| 24 | 40 | 29 | 95 | 91:9 | 82 |
| 48 | 40 | 33 | 98 | 88:12 | 76 |
| 72 | 40 | 35 | 96 | 89:11 | 78 |
| 48 | 40 | 42 | 97 | 87:13 | 74 |
| 48 | 40 | 44 | 92 | 87:13 | 74 |
| 48 | 40 | 53 | 88 | 85:15 | 70 |

EXAMPLE 3

*Pseudomonas cepacia* Lipase-Catalyzed Aminolysis of Racemic Isobutyl 2-[3-(4-Cyanophenyl)-4,5-Dihydro-5-Isoxazolyl]Acetate The procedure in Example 1 was repeated, except that 45 g/mL of (Amano PS30) lipase and 20 mg/mL of 3A powdered, activated molecular sieves were used in all reactions, and the initial reaction temperature was maintained at 24° C. for 24 h (to allow the powdered, activated 3 Å molecular sieves to remove water from the reaction mixture), then increased to 40° C. for an additional 24 h to 48 h (to increase the reaction rate). The results are summarized in Table 3.1.

TABLE 3.1

Enantioselective Amination of (R/S)-2 using *Pseudomonas cepacia* Lipase

| time[a] (h) | temp.[a] (° C.) | (R/S)-2 conv. (%) | (R,S)-1 + (S,S)-1 sel. (%) | (R,S)-1: (S,S)-1 | (R,S)-1 de (%) |
|---|---|---|---|---|---|
| 24 | 40 | 12 | 94 | 93:7 | 86 |
| 48 | 40 | 20 | 97 | 91:9 | 82 |
| 48 | 40 | 28 | 96 | 92:8 | 84 |
| 48 | 40 | 33 | 95 | 90:10 | 80 |

[a]time and temperature after allowing reaction to proceed for 24 h at 24° C.

EXAMPLE 4

Pseudomonas cepacia Lipase-Catalyzed Aminolysis of Racemic Isobutyl 2-[3-(4-Cyanophenyl)-4,5-Dihydro-5-Isoxazolyl]Acetate The procedure in Example 1 was repeated using methyl-t-butyl ether as solvent instead of diisopropyl ether, and reactions contained 20–30 mg/mL of 3A powdered, activated molecular sieves. The results are summarized in Table 4.1.

TABLE 4.1

Enantioselective amination of (R/S)-2 using *Pseudomonas cepacia* Lipase

| time (h) | temp. (° C.) | 3Å sieves (mg/mL) | (R/S)-2 conv. (%) | (R,S)-1 + (S,S)-1 sel. (%) | (R,S)-1: (S,S)-1 | (R,S)-1 de (%) |
|---|---|---|---|---|---|---|
| 72 | 24 | 30 | 14 | 96 | 93:7 | 86 |
| 72 | 24 | 20 | 17 | 97 | 92:8 | 84 |
| 72 | 24 | 20 | 19 | 99 | 91:9 | 82 |
| 72 | 24 | 25 | 24 | 95 | 91:9 | 82 |

EXAMPLE 5

*Pseudomonas cepacia* Lipase-Catalyzed Aminolysis of Racemic Isobutyl 2-[3-(4-Cyanophenyl)-4,5-Dihydro-5-Isoxazolyl]Acetate The procedure in Example 1 was repeated using methyl-t-butyl butyl ether as solvent instead of diisopropyl ether, and reactions contained 20–25 mg/mL of 3 Å powdered, activated molecular sieves and 60 mg/mL of *Pseudomonas cepacia* (Amano PS30) lipase. The initial reaction temperature was maintained at 24° C. for 24 h (to allow the powdered, activated 3 Å molecular sieves to remove water from the reaction mixture), then increased to 40° C. for an additional 24 h to 48 h (to increase the reaction rate). The results are summarized in Table 5.1.

TABLE 5.1

Enantioselective Amination of (R/S)-2 using *Pseudomonas cepacia* Lipase

| time[a] (h) | temp.[a] (° C.) | 3Å sieves (mg/mL) | (R/S)-2 conv. (%) | (R,S)-1 + (S,S)-1 sel. (%) | (R,S)-: (S,S)-1 | (R,S)-1 de (%) |
|---|---|---|---|---|---|---|
| 24 | 40 | 20 | 17 | 98 | 90:10 | 80 |
| 24 | 40 | 25 | 27 | 89 | 93:7 | 86 |
| 48 | 40 | 25 | 30 | 90 | 91:9 | 82 |
| 24 | 40 | 20 | 35 | 89 | 92:8 | 84 |
| 24 | 40 | 25 | 39 | 97 | 89:11 | 78 |
| 48 | 40 | 20 | 46 | 88 | 89:11 | 78 |
| 48 | 40 | 25 | 52 | 90 | 85:15 | 70 |

[a]time and temperature after allowing reaction to proceed for 24 h at 24° C.

EXAMPLE 6

*Pseudomonas cepacia* Lipase-Catalyzed Aminolysis of Racemic Isobutyl 2-[3-(4-Cyanophenyl)-4,5-Dihydro-5-Isoxazolyl]Acetate The procedure in Example 1 was repeated at either 24° C. or 40° C. using heptane as solvent instead of diisopropyl ether, and reactions contained 20 mg/mL of 3 Å powdered, activated molecular sieves. The results are summarized in Table 6.1.

TABLE 6.1

Enantioselective Amination of (R/S)-2 using *Pseudomonas cepacia* Lipase

| time (h) | temp. (° C.) | (R/S)-2 conv. (%) | (R,S)-1 + (S,S)-1 sel. (%) | (R,S)-1: (S,S)-1 | (R,S)-1 de (%) |
|---|---|---|---|---|---|
| 72 | 24 | 12 | 94 | 83:17 | 66 |
| 72 | 40 | 24 | 90 | 86:14 | 72 |

EXAMPLE 7

*Candida antartica* Lipase B-Catalyzed Aminolysis of Racemic Isobutyl 2-[3-(4-Cyanophenyl)-4,5-Dihydro-5-Isoxazolyl]Acetate The procedure in Example 1 was repeated using 30 mg of *Candida antartica* Lipase B instead of *Pseudomonas cepacia* (Amamo PS30) lipase (prepared in buffer and lyophilized as described for PS30 lipase), methyl-t-butyl ether as solvent instead of diisopropyl ether, and 20 mg/mL of 3 Å powdered, activated molecular sieves. The results are summarized in Table 7.1.

TABLE 7.1

Enantioselective Amination of (R/S)-2 using *Candida antartica* Lipase B

| time (h) | temp. (° C.) | (R/S)-2 conv. (%) | (R,S)-1 + (S,S)-1 sel. (%) | (R,S)-1: (S,S)-1 | (R,S)-1 de (%) |
|---|---|---|---|---|---|
| 24 | 24 | 11 | 88 | 94:6 | 88 |
| 24 | 24 | 31 | 81 | 96:4 | 92 |

EXAMPLE 8

*Candida antartica* Lipase A-Catalyzed Aminolysis of Racemic Isobutyl 2-[3-(4-Cyanophenyl)-4,5-Dihydro-5-Isoxazolyl]Acetate Comparative Example The procedure in Example 7 was repeated using *Candida antartica* Lipase A instead of *Candida antartica* Lipase B, producing the undesired (S,S)-1 diastereomer. The results are summarized in Table 8.1.

TABLE 8.1

Enantioselective Amination of (R/S)-2 using *Candida antartica* Lipase A

| time (h) | temp. (° C.) | (R/S)-2 conv. (%) | (R,S)-1 + (S,S)-1 sel. (%) | (R,S)-1: (S,S)-1 | (R,S)-1 de (%) |
|---|---|---|---|---|---|
| 24 | 24 | 35 | 86 | 12:88 | 76 |

What is claimed is:

1. A process for the enantioselective enzymatic aminolysis of racemic 2-[3-(4-cyanophenyl)-4,5-dihydro-5-isoxazolyl]acetate ((R/S)-I),

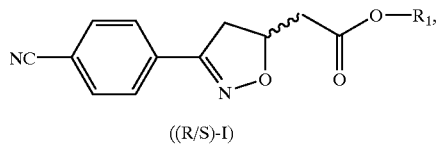

((R/S)-I)

wherein $R_1$ is selected from the group comprising of unsubstituted or substituted $C_1$–$C_6$ alkyl or alkenyl, $C_3$–$C_6$ cycloalkyl, substituted or unsubstituted aryl, substituted or unsubstituted arylalkyl, or substituted or unsubstituted heteroaryl alkyl, by methyl $N_\alpha$-Boc-L-αβ-diaminoproprionate.p-toluene-sulfonic acid, (S)-4, (S)-4 to produce (R)-methyl-3-[[[3-(4-cyanophenyl)-4,5-dihydro-5-isoxazolyl]acetyl]amino]-N-(butoxycarbonyl)-L-alanine, ((R,S)-1), (R, S)-1 comprising:
(a) contacting racemic ((R/S)-I) with a compound of formula (S)-4, an effective amount of enzyme catalyst which is optionally immobilized on an insoluble organic or inorganic carrier, an organic solvent, and optionally a desiccant, in a reaction mixture to form a compound of formula (R,S)-1; and
(b) isolating the compound of formula (R,S)-1 from the reaction mixture of step (a).

2. The process of claim 1 wherein, in step (a), the enzyme catalyst is selected from the group comprising of *Pseudomonas cepacia* lipase and *Candida antartica* lipase fraction B.

3. The process of claim 1 wherein, in step (a), the enzyme catalyst has an adjusted pH of from about 7.0 to about 10.0.

4. The process of claim 1 wherein, in step (a), the desiccant comprises of activated 3 Å molecular sieves or activated 4 Å molecular sieves.

5. The process of claim 1 wherein, in step (a), the organic solvent is selected from the group comprising of methyl-t-butyl ether, diisopropyl ether, heptane, toluene, 1,4-dioxane, and acetonitrile.

6. The process of claim 1 wherein, in step (a), the temperature of the reaction mixture is from about 0° C. to about 60° C.

7. The process of claim 1, wherein $R_1$ is selected from the group comprising of unsubstituted or substituted $C_1$–$C_4$ alkyl, $C_3$–$C_6$ cycloalkyl, and substituted or unsubstituted aryl, and in step (a)
the enzyme catalyst is selected from the group comprising of *Pseudomonas cepacia* lipase and *Candida antartica* lipase fraction B and has an adjusted pH of about 7.0 to about 10.0;

the temperature of the reaction mixture is from about 0° C. to about 60° C.;

the organic solvent is selected from the group comprising of methyl-t-butyl ether, diisopropyl ether, heptane, toluene, 1,4-dioxane, and acetonitrile; and the desiccant comprises of activated 3 Å molecular sieves or activated 4 Å molecular sieves.

8. The process of claim 7, wherein $R_1$ is selected from the group comprising of unsubstituted or substituted $C_1$–$C_4$ alkyl, and in step (a)

the enzyme catalyst is selected from the group comprising of *Pseudomonas cepacia* lipase and *Candida antartica* lipase fraction B and has an adjusted pH of from about 7.5 to about 9.5;

the temperature of the reaction mixture is from about 10° C. to about 60° C.; and the organic solvent is selected from the group comprising of methyl-t-butyl ether, diisopropyl ether, and heptane.

9. The process of claim 8, wherein $R_1$ is isobutyl, and in step (a)

the enzyme catalyst is selected from the group comprising of *Pseudomonas cepacia* lipase and *Candida antartica* lipase fraction B and has an adjusted pH of about 8 to 8.5; and the temperature of the reaction mixture is from about 20° C. to about 40° C.

10. The process for the enantioselective enzymatic aminolysis of racemic 2-[3-(4-cyanophenyl)-4,5-dihydro-5-isoxazolyl]acetate ((R/S)-I),

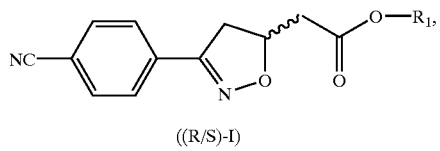

((R/S)-I)

wherein $R_1$ is selected from the group comprising of unsubstituted or substituted $C_1$–$C_6$ alkyl or alkenyl, $C_3$–$C_6$ cycloalkyl, substituted or unsubstituted aryl, substituted or unsubstituted arylalkyl, or substituted or unsubstituted heteroaryl alkyl, by methyl $N_\alpha$-Boc-L-$\alpha\beta$-diaminoproprionate.p-toluenesulfonic acid, (S)-4,

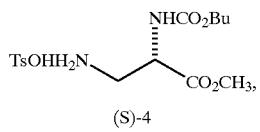

(S)-4 to produce (R)-methyl-3-[[[3-(4-cyanophenyl)-4,5-dihydro-5-isoxazolyl]acetyl]amino]-N-(butoxycarbonyl)-L-alanine, ((R,S)-1),

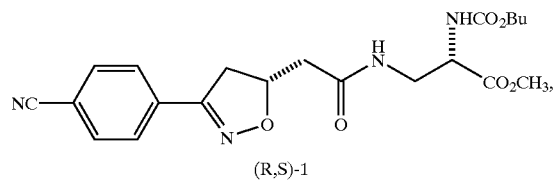

(R,S)-1 further comprising:

(a) contacting racemic ((R/S)-I) with a compound of formula (S)-4, an effective amount of enzyme catalyst which is optionally immobilized on an insoluble organic or inorganic carrier, an organic solvent, and optionally a desiccant, in a reaction mixture to form a compound of formula (R,S)-1; and (b) isolating the compound of formula (R,S)-1 from the reaction mixture of step (a);

(c) isolating unreacted S-enantiomer ((S)-I)

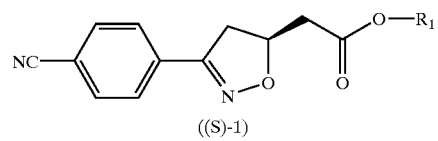

((S)-1)

from the reaction mixture of step(b);

(c) heating the unreacted S-enantiomer ((S)-I) obtained from step (c) in toluene in the presence of a catalytic amount of potassium tert-butoxide to yield racemic 2-[3-(4-cyanophenyl)-4,5-dihydro-5-isoxazolyl]-acetate ((R/S)-I); and (e) recycling the racemic 2-[3-(4-cyanophenyl)-4,5-dihydro-5-isoxazolyl]acetate ((RIS)-I) obtained from step (d) by applying steps (a) to (e);

the recycling step (e) is performed from 1 to 5 times.

11. The process of claim 10, wherein $R_1$ is selected from the group comprising of unsubstituted or substituted $C_1$–$C_4$ alkyl, $C_3$–$C_6$ cycloalkyl, and substituted or unsubstituted aryl, and in step (a)

the enzyme catalyst is selected from the group comprising of *Pseudomonas cepacia* lipase and *Candida antartica* lipase fraction B and has an adjusted pH of about 7.0 to about 10.0;

the temperature of the reaction mixture is from about 0° C. to about 60° C.;

the organic solvent is selected from the group comprising of methyl-t-butyl ether, diisopropyl ether, heptane, toluene, 1,4-dioxane, and acetonitrile; and the desiccant comprises of activated 3 Å molecular sieves or activated 4 Å molecular sieves.

12. The process of claim 11, wherein $R_1$ is selected from the group comprising of unsubstituted or substituted $C_1$–$C_4$ alkyl, and in step (a)

the enzyme catalyst is selected from the group comprising of *Pseudomonas cepacia* lipase and *Candida antartica* lipase fraction B and has an adjusted pH of from about 7.5 to about 9.5;

the temperature of the reaction mixture is from about 10° C. to about 60° C.; and the organic solvent is selected from the group comprising of methyl-t-butyl ether, diisopropyl ether, and heptane.

13. The process of claim 12, wherein $R_1$ is isobutyl, and in step (a)

the enzyme catalyst is selected from the group comprising of *Pseudomonas cepacia* lipase and *Candida antartica* lipase fraction B and has an adjusted pH of about 8 to 8.5; and the temperature of reaction mixture is from about 20° C. to about 40° C.

14. A process for the preparation of (R)-methyl-3-[[[3-[4-(aminoiminomethyl) phenyl]-4,5-dihydro-5-isoxazolyl] acetyl]amino]-N-(butoxycarbonyl)-L-alanine monoacetate (roxifiban)

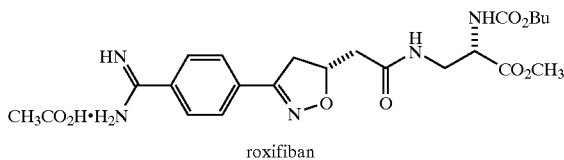

roxifiban comprising:
(a) contacting racemic 2-[3-(4-cyanophenyl)-4,5-dihydro-5-isoxazolyl]acetate ((RIS)-I),

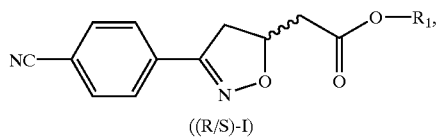

((R/S)-I)

wherein $R_1$ is selected from the group comprising of unsubstituted or substituted $C_1$–$C_6$ alkyl or alkenyl, $C_3$–$C_6$ cycloalkyl, substituted or unsubstituted aryl, substituted or unsubstituted arylalkyl, or substituted or unsubstituted heteroaryl alkyl,
with methyl $N_\alpha$-Boc-L-αβ-diaminoproprionate.p-toluenesulfonic acid, (S)-4,

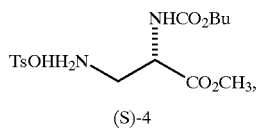

(S)-4 which is optionally immobilized on an insoluble organic or inorganic carrier, an organic solvent, and optionally a desiccant, in a reaction mixture to form a compound of formula (R,S)-1, (R)-methyl-3-[[[3-(4-cyanophenyl)-4,5-dihydro-5-isoxazolyl]acetyl]amino]-N-(butoxycarbonyl)-L-alanine,

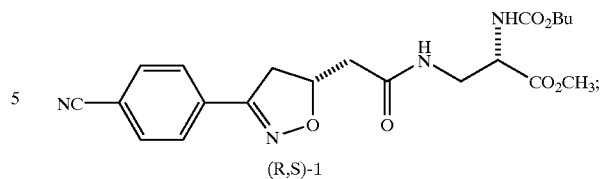

(R,S)-1

(b) isolating the compound of formula (R,S)-1 from the reaction mixture of step (a);
(c1) contacting the compound of formula (R,S)-1, isolated in step (b) with HCl and methanol in methyl acetate to form an imidate compound,

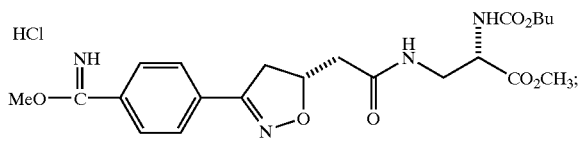

(d1) contacting the imidate compound produced in step (c1) with ammonium acetate to produce R)-methyl-3-[[[3-[4-(aminoiminomethyl)phenyl]-4,5-dihydro-5-isoxazolyl]acetyl]amino]-N-(butoxycarbonyl)-L-alanine monoacetate; and
(e1) recovering the product of step (d1).

15. The process of claim 14, wherein in step (a), $R_1$ is selected from the group comprising of unsubstituted or substituted $C_1$–$C_4$ alkyl, $C_3$–$C_6$ cycloalkyl, and substituted or unsubstituted aryl.

16. The process of claim 15, wherein in step (a), $R_1$ is selected from the group comprising of unsubstituted or substituted $C_1$–$C_4$ alkyl.

17. The process of claim 16, wherein in step (a), $R_1$ is isobutyl.

* * * * *